United States Patent [19]

Nakamura et al.

[11] 4,306,088
[45] Dec. 15, 1981

[54] PRODUCTION OF METHACROLEIN

[75] Inventors: Shuzo Nakamura, Osaka; Hiroshi Ichihashi, Niihama; Yoshihiko Nagaoka, Niihama; Koichi Nagai, Niihama, all of Japan

[73] Assignee: Sumitomo Chemical Company, Limited, Osaka, Japan

[21] Appl. No.: 162,883

[22] Filed: Jun. 25, 1980

[30] Foreign Application Priority Data

Jul. 9, 1979 [JP] Japan .................. 54-87281

[51] Int. Cl.$^3$ ............... C07C 45/35; C07C 45/32; C07C 47/22
[52] U.S. Cl. .................. 568/471; 568/481; 568/479; 568/480
[58] Field of Search ............ 568/474, 479, 471, 481, 568/480

[56] References Cited

U.S. PATENT DOCUMENTS

| 3,522,299 | 7/1970 | Takenaka et al. | 568/479 |
| 4,012,449 | 3/1977 | Shikakura et al. | 568/471 |
| 4,035,418 | 7/1977 | Okada et al. | 568/471 |
| 4,111,984 | 9/1978 | Ishii et al. | 568/471 |
| 4,230,639 | 10/1980 | Khoobiar | 568/471 |

FOREIGN PATENT DOCUMENTS 50-62523 5/1975 Japan.

OTHER PUBLICATIONS

"New Route to Methyl Methacrylate", by Yoshio Oda et al., Hydrocarbon Processing, Oct. 1975, pp. 115–117.
"Oxidation of Isobutene to Methacrolein Over U–Sb and Bi–Mo Oxide Catalysts", by Yoshiro Morita et al., Bulletin of the Japan Petroleum Institute, pp. 71–75.
"Recent Progress in Oxidation Catalysts for $C_{3-4}$ Olefins from the Patent Aspects", by Takashi Ohara, Shokubai, vol. 19, No. 3 (1977).

Primary Examiner—Werren B. Lone
Attorney, Agent, or Firm—Birch, Stewart, Kolasch and Birch

[57] ABSTRACT

In the production of methacrolein by vapor phase catalytic oxidation of isobutylene and/or t-butyl alcohol, an improved process for suppressing the amount of acetone to be by-produced which comprises contacting a gaseous mixture comprising isobutylene or t-butyl alcohol, molecular oxygen and steam with a metal oxide catalyst composition comprising molybdenum and bismuth as the essential metal components, the amount of steam in the gaseous mixture being kept to be not more than 4 mol per mol of isobutylene or not more than 3 mol per mol of t-butyl alcohol.

11 Claims, 1 Drawing Figure $H_2O$/Isobutylene (molar ratio)

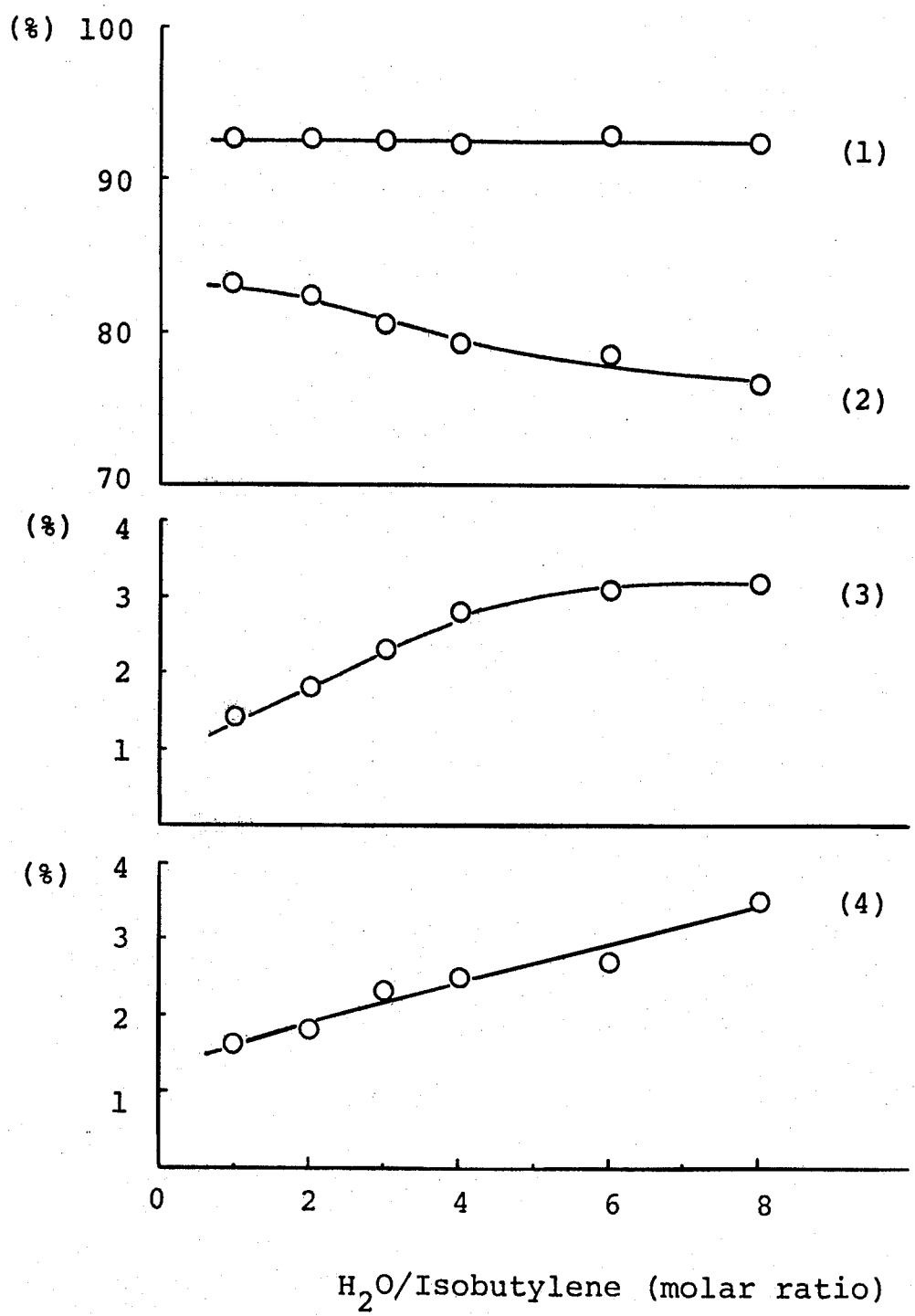

PRODUCTION OF METHACROLEIN

The present invention relates to improvements in the production of methacrolein. More particularly, it relates to a process for preparing methacrolein with suppression of the by-production of acetone by vapor phase catalytic oxidation of isobutylene or t-butyl alcohol.

In the vapor phase catalytic oxidation of isobutylene or t-butyl alcohol for production of methacrolein, the introduction of steam into the reaction system has heretofore been considered to be essential for facilitating the control of the reaction and enhancing the yield of methacrolein (Ohara; Shokubai, 19, 157–163 (1977)). Based on the above consideration, steam has been usually introduced in the reaction system as a diluent in such a large amount as 6 mol or more, particularly 8 mol or more, per mol of isobutylene or t-butyl alcohol.

On the other hand, the most important use of methacrolein from the industrial viewpoint is production of methacrylic acid by its vapor phase catalytic oxidation. For such vapor phase catalytic oxidation, there are known several procedures, among which the supply of purified methacrolein to a reactor for manufacture of methacrylic acid (Oda et al.: Hydrocarbon Processing, 115–117, October (1975)) is included. This procedure is said to be effective in preventing the produced gaseous mixture from coming within the range of explosive composition. The present inventors consider that the introduction of methacrolein without purification may afford an unfavorable influence on the life of the catalyst for production of methacrylic acid and results in decrease of the yield of methacrylic acid. If the vapor phase catalytic oxidation of isobutylene or t-butyl alcohol can afford methacrolein in high purity or with only negligible amounts of by-products, it will be made possible to introduce the reaction mixture containing methacrolein directly into a reactor for production of methacrylic acid without any intermediary purification step.

For the vapor phase catalytic oxidation of isobutylene or t-butyl alcohol to methacrolein, there is frequently used a metal oxide catalyst composition comprising molybdenum and bismuth. In such cases, acetone is always by-produced in an amount of several percent in addition to other by-products such as carbon monoxide, carbon dioxide, acetic acid, etc. Among various by-products, acetone affords a particularly unfavorable influence on the vapor phase oxidation of methacrolein in the presence of a mixed oxide catalyst containing molybdenum or a heteropolymolybdate catalyst. Therefore, the elimination or decrease of acetone from the methacrolein-containing product has been demanded for its use as the starting material for production of methacrylic acid.

As the result of an extensive study for suppressing the by-production of acetone, it has been found that the introduction of a large amount of steam as a diluent into the reaction system, which has heretofore been considered to be essential, is rather unfavored in promoting the by-production of acetone, and the control of the amount of steam to be introduced below a certain limit decreases remarkably the amount of acetone by-produced.

Referring to the FIGURE of the accompanying drawing showing the variation of the results with the replacement of steam to be introduced as a diluent into the reaction system for vapor phase catalytic reaction of isobutylene to produce methacrolein partly by carbon dioxide, which was drafted by plotting the results obtained in Examples 1 to 4 and reference Examples 1 to 2 as hereinafter described on a graph of which the axis of abscissa indicates the value X when the composition of the gaseous mixture as the starting material is varied with the conditions of isobutylene:air:steam:carbon dioxide = 1:15:X:Y (by molar ratio) and X+Y=8 and the ordinate indicates the conversions and the yields, the curves (1) to (4) show respectively the conversion of isobutylene, the yield of methacrolein, the selectivity to acetone and the selectivity to acetic acid. As understood from the said FIGURE, the amount of acetone to be by-produced is significantly decreased when the amount of steam to be introduced into the reaction system is 4 mol or less per mol of isobutylene. In this case, it is also understood that the use of steam in such proportion can simultaneously decrease the by-produced amount of acetic acid and increase the yield of methacrolein.

When t-butyl alcohol is used in place of isobutylene, there is produced in situ 1 mol of water per mol of t-butyl alcohol according to the following formula:

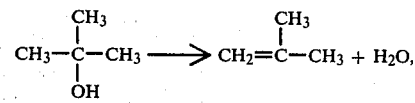

and therefore the amount of steam to be introduced may be 3 mol or less per mol of t-butyl alcohol for decreasing the amount of acetone to be by-produced.

According to the present invention, there is provided an improved process for preparation of methacrolein by vapor phase catalytic oxidation of isobutylene and/or t-butyl alcohol which comprises contacting a gaseous mixture comprising isobutylene or t-butyl alcohol, molecular oxygen and steam with a metal oxide catalyst composition comprising molybdenum and bismuth as the essential metal components, the amount of steam in the gaseous mixture being kept to be not more than 4 mol per mol of isobutylene or not more than 3 mol per mol of t-butyl alcohol, whereby the amount of acetone to be by-produced is suppressed.

The catalyst to be used in the process of this invention is a metal oxide catalyst composition comprising molybdenum and bismuth as the essential metal components. Particularly effective is a metal oxide catalyst composition comprising molybdenum, bismuth and iron as the essential metal components. Thus, a metal oxide catalyst composition comprising the metal components corresponding to the following formula may be favorably employed: Mo-Bi-Fe-X-Y-Z wherein X is at least one of Ni, Co, Mg, Mn, Cr, W, Sn and Cu, Y is at least one of P, Sb, B and Te and Z is K, Rb, Cs and Tl, Y and Z being optional. Usually, the catalyst is employed with a carrier, of which examples are silica, alumina, titania, zirconia, etc. These metal oxide catalyst compositions and carriers are well known and conventional.

The gaseous mixture as the starting material comprises isobutylene or t-butyl alcohol, molecular oxygen and steam. The molar ratio between isobutylene or t-butyl alcohol and molecular oxygen may be 1:2.0–4.5. As stated above, steam should be used in an amount of 4 mol or less, preferably 3 mol or less, to 1 mol of isobutylene and in an amount of 3 mol or less, preferably 2 mol or less, to 1 mol of t-butyl alcohol. No lower limit is present on the amount of steam, and any trace amount of steam is acceptable. When t-butyl alcohol is used, there is produced water in situ in the reaction system, and therefore any intentional incorporation of steam into the gaseous mixture is not necessarily required. In other words, t-butyl alcohol may be considered to be substantially equal to an equimolar amount of isobutylene and water in the reaction system of the process of this invention. Further, t-butyl alcohol forms an azeotropic mixture with water in a molar ratio of about 1:1. Such azeotropic mixture is available at a low cost in comparison with pure t-butyl alcohol, and its use is favorable from the industrial viewpoint.

In place of isobutylene or t-butyl alcohol alone, there may be used their mixture. In such case, the amount of molecular oxygen or of steam to be used may be the sum of the ones respectively determined on isobutylene and t-butyl alcohol on the basis of the said proportions. Still, the presecnce of small amounts of such saturated hydrocarbons as methane, propane and butane or carbon monoxide in the gaseous mixture does not substantially prevent the catalytic oxidation.

On the industrial application of the process of this invention, the gaseous mixture should be kept outside the range for explosive compositions. In order to assure this, an inert gas such as nitrogen or carbon dioxide may be incorporated as a diluent into the gaseous mixture. Among various inert gases, the use of carbon dioxide is favorable due to its large specific heat. Advantageously, carbon dioxide is readily available at low cost, because it is included in a large amount in exhaustive gas from various chemical plants. Since carbon dioxide as a diluent may contain any other inert gas such as nitrogen and small amounts of oxygen and carbon monoxide, the exhaustive gas from an apparatus such as a heating furnace or a boiler wherein the so-called "clean fuel" not containing any sulfurous material is used may be as such employed as a diluent. The exhaustive gas from a reactor for vapor phase catalytic oxidation of isobutylene or t-butyl alcohol may be also used as a diluent. Such inert diluent gas other than steam may be used in the molar ratio of from 10 to 40 mol per mol of isobutylene of t-butyl alcohol and of from 3.8 to 10 mol per mol of molecular oxygen.

The reaction temperature may be usually from 300° to 450° C. The space velocity of the gaseous mixture as the starting material is normally from 500 to 6000 hr$^{-1}$. The pressure in a reactor is preferred to be around the atmospheric pressure, particularly 4 kg/cm$^2$ in gauge pressure or less.

The thus produced methacrolein is much decreased in the contaminating amounts of acetone and acetic acid and can be used as such as the starting material for production of methacrylic acid. In other words, this invention makes possible the direct connection of a reactor for oxidation of methacrolein to methacrylic acid to a reactor for oxidation of isobutylene or t-butyl alcohol to methacrolein, whereby the continuous production of methacrylic acid from isobutylene or t-butyl alcohol via methacrolein can be accomplished without any intermediary purification step. Still, the process of this invention is effective in enhancing the yield of methacrolein and improving the life of the catalyst.

Throughout this specification, the conversion of isobutylene or t-butyl alcohol, the yield of methacrolein, the selectivity to acetone and the selectivity to acetic acid are calculated according to the following equations:

Conversion of isobutylene or t-butyl alcohol (%) =
$$\frac{\text{Reacted isobutylene or t-butyl alcohol (mol)}}{\text{Feed isobutylene or t-butyl alcohol (mol)}} \times 100$$

Yield of methacrolein (%) = $\frac{\text{Produced methacrolein (mol)}}{\text{Feed isobutylene or t-butyl alcohol (mol)}} \times 100$ Selectivity to acetone (%) = $\frac{\text{Produced acetone (mol)}}{\text{Reacted isobutylene or t-butyl alcohol (mol)}} \times \frac{3}{4} \times 100$ Selectivity to acetic acid (%) =
$\frac{\text{Produced acetic acid (mol)}}{\text{Reacted isobutylene or t-butyl alcohol (mol)}} \times \frac{2}{4} \times 100$ Practical and presently preferred embodiments of the invention are illustratively shown in the following Examples.

EXAMPLES 1–4 AND REFERENCE EXAMPLES 1–2

Bismuth nitrate (12.13 g) was dissolved in a mixture of conc. nitric acid (60% by weight; 4 ml) and water (30 ml), and a solution of ferric nitrate (20.20 g), cobalt nitrate (29.12 g), nickel nitrate (36.42 g) and thallium nitrate (3.33 g) in water (250 ml) was added thereto. To the resultant mixture, a solution obtained by dissolving ammonium paramolybdate (52.98 g) in a mixture of ammonia water (28% by weight; 30 ml) and water (300 ml) and adding phosphoric acid (85% by weight; 0.95 g) thereto was added to give a suspension. To the suspension, silica sol (100 ml) containing 20% by weight of SiO$_2$ was added, and vigorous stirring was effected. The resultant suspension was evaporated to dryness, and the residue was calcined in air at 300° C. for 3 hours and cooled, followed by crushing. The obtained crushed product was shaped by the use of a tabletting machine into tablets, and the tablets were calcined at 550° C. for 6 hours. The thus prepared catalyst had the following composition: Mo$_{12}$Bi$_1$Fe$_2$Ni$_5$Co$_4$Tl$_{0.5}$P$_{0.4}$O$_{50.8}$·15SiO$_2$.

The catalyst was pulverized, and particles of 24 to 32 mesh size (2 g) was admixed with fused alumina (Alundum) (24–32 mesh; 18 ml). The mixture was charged in a glass made reactor of 15 mm in inner diameter. The reactor was heated in an electric furnace to adjust the temperature of the catalyst layer to 380° C. The gaseous mixture having the composition as shown in Table 1 was fed into the reactor with a space velocity of 5000 h$^{-1}$.

The results are shown in Table 1 and also graphed in the FIGURE of the accompanying drawing. In the FIGURE, the axis of abscissa indicates the molar ratio of steam to isobutylene, and the ordinate indicates conversions and yields. The curves (1) to (4) show respectively the conversion of isobutylene, the yield of methacrolein, the selectivity to acetone and the selectivity to acetic acid.

TABLE 1

| Feed gas composition Isobutylene: air:CO$_2$:H$_2$O (molar ratio) | Isobutylene conversion (%) | Methacrolein yield (%) | Acetone selectivity (%) | Acetic acid selectivity (%) |
| --- | --- | --- | --- | --- |
| Example 1   1:15:7:1 | 92.7 | 82.7 | 1.5 | 1.6 |
| Example 2   1:15:6:2 | 92.6 | 82.4 | 1.8 | 1.8 |
| Example 3   1:15:5:3 | 92.5 | 80.6 | 2.3 | 2.3 |
| Example 4   1:15:4:4 | 92.4 | 79.2 | 2.8 | 2.5 |
| Reference   1:15:2:6 | 93.1 | 78.5 | 3.1 | 2.7 |

TABLE 1-continued

| | Feed gas composition Isobutylene: air:CO$_2$:H$_2$O (molar ratio) | Isobutylene conversion (%) | Methacrolein yield (%) | Acetone selectivity (%) | Acetic acid selectivity (%) |
|---|---|---|---|---|---|
| Example 1 Reference Example 2 | 1:15:0:8 | 92.5 | 76.7 | 3.2 | 3.5 |

EXAMPLE 5

As in Example 1 but using a gaseous mixture having a composition of isobutylene:air:nitrogen:steam = 1:15:6:2 (by mol), the reaction was carried out. The results were as follows: conversion of isobutylene, 92.6%; yield of methacrolein, 82.6%; selectivity to acetone, 1.9%; selectivity to acetic acid, 1.8%.

In comparison of this Example with Example 2, the results are substantially identical, and it is understood that the use of carbon dioxide as a diluent affords substantially the same results as the use of nitrogen as a diluent does. Namely, the effect for decreasing the yield of acetone as shown in Examples 1 to 4 is not due to the use of carbon dioxide as a diluent but due to keeping the amount of steam within a range of H$_2$O/isobutylene $\leq$ 4.

EXAMPLE 6

The same catalyst as used in Example 1 (10 ml) was charged in a glass made reactor of 15 mm in inner diameter and heated with an electric furnace to adjust the temperature of the catalyst layer to 360° C. Then, a gaseous mixture having a composition of isobutylene:air:carbon dioxide:steam = 1:15:6:2 (by mol) was fed into the reactor with a space velocity of 1500 hr$^{-1}$, and the reaction was carried out for a period of 61 consecutive days.

After one day from the start of the reaction, the results were as follows: conversion of isobutylene, 98.7%; yield of methacrolein, 81.7%; selectivity to acetone, 2.7%. After 61 days from the start of the reaction, the results were as follows: conversion of isobutylene, 98.5%; yield of methacrolein, 82.3%; selectivity to acetone, 2.7%. These results are shown in Table 2 together with the results at some other stages.

On the basis of the above results, the relationship between the number of days after the start of the reaction (X) and the obtained results are shown by the following equations according to the method of least squares:

Conversion of isobutylene
(%) = 98.6 − 0.006$X$($\gamma$ = −0.31)

Yield of methacrolein (%) = 81.8 + 0.01$X$($\gamma$ = +0.56)

wherein $\gamma$ is a coefficient of correlation between the number of days after the start of the reaction and the obtained results. The coefficient of correlation on the conversion of isobutylene is −0.31, and the correlation with the depression of the activity may be considered to be low.

TABLE 2

| Days | Isobutylene conversion (%) | Methacrolein yield (%) | Acetone selectivity (%) |
|---|---|---|---|
| 1 | 98.7 | 81.7 | 2.7 |
| 3 | 99.2 | 81.9 | 2.7 |
| 6 | 98.9 | 81.6 | 2.7 |
| 10 | 98.6 | 82.9 | 2.6 |
| 13 | 98.5 | 81.9 | 2.7 |
| 17 | 97.9 | 81.3 | 2.7 |
| 22 | 98.3 | 81.9 | 2.7 |
| 27 | 98.0 | 81.0 | 2.7 |
| 31 | 98.6 | 82.6 | 2.8 |
| 34 | 97.9 | 81.3 | 2.7 |
| 37 | 98.3 | 82.1 | 2.6 |
| 41 | 98.5 | 82.4 | 2.7 |
| 45 | 98.0 | 82.3 | 2.7 |
| 48 | 98.6 | 82.6 | 2.7 |
| 50 | 98.0 | 80.9 | 2.7 |
| 51 | 98.7 | 81.9 | 2.7 |
| 55 | 98.9 | 82.3 | 2.7 |
| 59 | 98.0 | 82.5 | 2.7 |
| 61 | 98.5 | 82.3 | 2.7 |

EXAMPLE 7

Bismuth nitrate (12.13 g) was dissolved in a mixture of conc. nitric acid (60% by weight; 4 ml) and water (30 ml), and a solution of ferric nitrate (101.0 g), cobalt nitrate (29.12 g), nickel nitrate (36.42 g) and thallium nitrate (3.33 g) in water (350 ml) was added thereto. To the resultant mixture, a solution obtained by dissolving ammonium paramolybdate (52.98 g) in a mixture of ammonia water (28% by weight; 30 ml) and water (300 ml) and adding phosphoric acid (85% by weight; 1.15 g) thereto was added, followed by stirring to give a suspension. To the suspension, silica gel (100 ml) containing 20% by weight of SiO$_2$ was added, and vigorous stirring was effected. The resultant suspension was evaporated to dryness, and the residue was calcined in air at 300° C. for 3 hours and cooled, followed by crushing. The obtained crushed product was shaped by the use of a tabletting machine into tablets, and the tablets were calcined at 550° C. for 6 hours. The thus prepared catalyst had the following composition: Mo$_{12}$Bi$_1$Fe$_{10}$Ni$_5$Co$_4$Tl$_{0.5}$P$_{0.4}$O$_{62.8}$.15SiO$_2$.

The catalyst was pulverized, and particles of 24 to 32 mesh size (2 g) was admixed with fused alumina (Alundum) (24–32 mesh; 18 ml). The mixture was charged in a glass made reactor of 15 mm in inner diameter. The reactor was heated in an electric furnace, and a gaseous mixture having a composition of isobutylene:air:nitrogen:steam = 1:15:6:2 (by mol) was fed into the reactor with a space velocity of 5000 hr−. The temperature in the reactor was adjusted to 420° C. at the maximum, and the reaction was carried out for a period of 14 consecutive days.

After one day from the start of the reaction, the results were as follows: conversion of isobutylene, 100%, yield of methacrolein, 82.4%. After 14 days from the start of the reaction, the results were as follows: conversion of isobutylene, 99.4%; yield of methacrolein, 82.5%.

On the basis of the above results together with the results after 4 days and 7 days from the start of the reaction, the relationship between the number of days after the start of the reaction (X) and the obtained results are shown by the following equations according to the method of least squares:

Conversion of isobutylene
(%) = 99.9 − 0.045$X$($\gamma$ = −0.82)

Yield of methacrolein
(%)=82.1+0.023X(γ= +0.43)

wherein γ is a coefficient of correlation between the number of days after the start of the reaction and the obtained results.

Still, the selectivity to acetone was always 0.8%.

EXAMPLE 8 AND REFERENCE EXAMPLE 3

As in Example 1 but using potassium nitrate (0.51 g) in place of thallium nitrate, the materials for preparation of the catalyst were mixed together. The resultant suspension was evaporated to dryness, and the residue was calcined in air at 300° C. for 3 hours and cooled, followed by crushing. The obtained crushed product was shaped by the use of a tabletting machine into tablets, and the tablets were calcined at 550° C. for 6 hours. The thus prepared catalyst had the following composition: $Mo_{12}Bi_1Fe_2Ni_5Co_4K_{0.2}P_{0.4}O_{50.6} \cdot 15SiO_2$.

The catalyst was pulverized, and particles of 24 to 32 mesh size (4.0 g) were admixed with fused alumina (Alundum) (24–32 mesh; 18 ml). The mixture was charged in a glass made reactor of 15 mm in inner diameter. The reactor was heated in an electric furnace, and a gaseous mixture having the composition as shown in Table 3 was fed into the reactor with a space velocity of 2500 hr$^{-1}$. The temperature of the catalyst layer was adjusted to 370° C. The results are shown in Table 3.

EXAMPLES 9–10 AND REFERENCE EXAMPLES 4–5

As in Example 1, there were prepared the catalysts having the following composition: $Mo_{12}Bi_1Fe_2Ni_9O_{49.5} \cdot 15SiO_2$ and $Mo_{12}Bi_1Fe_1Co_7K_{0.14}O_{46} \cdot 10SiO_2$. The calcined temperatures of the catalysts were respectively 650° C. and 600° C. As in Example 8, the reaction was carried out with a space velocity of 2500 hr$^{-1}$. The results are shown in Table 3.

EXAMPLE 11

As in Example 1, the materials for preparation of the catalyst were mixed together. The resultant suspension was evaporated to dryness, and the residue was calcined in air at 300° C. for 3 hours and cooled, followed by crushing to give particles having the following composition: $Mo_{12}Bi_1Fe_2Ni_5Co_4Tl_{0.5}P_{0.4}O_{50.8} \cdot 15SiO_2$. The particles were attached onto the surfaces of spherical carriers of about 5 mm in diameter (main component, α-alumina) by the use of a dish type granulator while rotating under spraying with water, dried and calcined in air at 550° C. for 6 hours. The thus obtained catalyst supports the active component in a weight of 30% by weight and has a spherical shape of about 5 mm in diameter.

The catalyst (12 ml) was charged in a glass made reactor of 15 mm in inner diameter, which was heated by an electric furnace to 420° C. A gaseous mixture having a composition of isobutylene:air:carbon dioxide:nitrogen:steam = 1:20:2:5:1 (by mol) was fed into the reactor with a space velocity of 1500 hr$^{-1}$, and the reaction was carried out.

The results were as follows: conversion of isobutylene, 92.0%; yield of methacrolein, 77.1%; selectivity to acetone, 2.7%; selectivity to acetic acid, 2.3%.

EXAMPLE 12

The same catalyst as used in Example 11 (12 ml) was charged into a glass made reactor of 15 mm in inner diameter, which was heated by an electric furnace to 420° C. A gaseous mixture having a composition of t-butyl alcohol:air:nitrogen:steam = 1:20:7:0.1 (by mol) was fed into the reactor with a space velocity of 1500 hr$^{-1}$. The results were as follows: conversion of t-butyl alcohol, 100%; yield of methacrolein, 77.8%; selectivity to acetone, 2.3%; selectivity to acetic acid, 2.1%.

EXAMPLE 13

As in Example 12 but using azeotropic t-butyl alcohol in place of pure t-butyl alcohol, the reaction was carried out. The composition of the gaseous mixture fed into the reactor was t-butyl alcohol:air:nitrogen:steam = 1:20:7:1.1 (by mol). The results were as follows: conversion of t-butyl alcohol, 100%; yield of methacrolein, 77.3%; selectivity to acetone, 2.5%; selectivity to acetic acid, 2.1%.

EXAMPLE 14

As in Example 12 but using a gaseous mixture having a composition of t-butyl alcohol:air:nitrogen:steam = 1:20:7:3 (by mol), the reaction was carried out.

TABLE 3

| | Catalyst compositions (molar ratio) | Reaction temperature (°C.) | Feed gas composition Isobutylene:air:N$_2$:H$_2$O | Isobutylene conversion (%) | Methacrolein yield (%) | Acetone selectivity (%) | Acetic acid selectivity (%) |
|---|---|---|---|---|---|---|---|
| Example 8 | $Mo_{12}Bi_1Fe_2Ni_5Co_4K_{0.2}P_{0.4}O_{50.6} \cdot 15\,SiO_2$ | 370 | 1:15:8:2 | 98.1 | 72.2 | 2.1 | 3.6 |
| Example 9 | $Mo_{12}Bi_1Fe_2Ni_9O_{49.5} \cdot 15\,SiO_2$ | 400 | 1:15:8:2 | 99.4 | 66.8 | 2.3 | 6.3 |
| Example 10 | $Mo_{12}Bi_1Fe_1Co_7K_{0.14}O_{46} \cdot 10\,SiO_2$ | 400 | 1:15:8:2 | 45.6 | 37.6 | 3.6 | 3.7 |
| Reference Example 3 | $Mo_{12}Bi_1Fe_2Ni_5Co_4K_{0.2}P_{0.4}O_{50.6} \cdot 15\,SiO_2$ | 370 | 1:15:0:10 | 99.5 | 62.9 | 3.7 | 6.6 |
| Reference Example 4 | $Mo_{12}Bi_1Fe_2Ni_9O_{49.5} \cdot 15\,SiO_2$ | 400 | 1:15:0:10 | 99.6 | 60.9 | 3.9 | 9.9 |
| Reference Example 5 | $Mo_{12}Bi_1Fe_1Co_7K_{0.14}O_{46} \cdot 10\,SiO_2$ | 400 | 1:15:0:10 | 51.4 | 35.1 | 5.9 | 6.4 |

In this case, a small amount of water was added to azeotropic t-butyl alcohol, i.e. a mixture of t-butyl alcohol and water in a molar ratio of 1:3, was used as the starting material. The results were as follows: conversion of t-butyl alcohol, 100%; yield of methacrolein, 76.0%; selectivity to acetone, 2.8%; selectivity to acetic acid, 2.4%.

What is claimed is:

1. In the production of methacrolein by vapor phase catalytic oxidation of isobutylene and/or t-butyl alcohol, an improved process for suppressing the amount of acetone to be by-produced which comprises contacting a gaseous mixture comprising isobutylene or t-butyl alcohol, molecular oxygen and steam with a metal oxide catalyst composition comprising metal components corresponding to the formula: Mo-Bi-Fe-X-Y-Z wherein X is at least one of Ni, Co, Mg, Mn, Cr, W, Sn or Cu, Y is at least one of P, B and Te and Z is at least one of K, Rb, Cs and Tl, the presence of Y and/or Z being optional, the amount of steam in the gaseous mixture being kept to be not more than 4 mol per mol of isobutylene or not more than 3 mol per mol of t-butyl alcohol.

2. The process according to claim 1, wherein the amount of steam in the gaseous mixture is not more than 3 mol per mol of isobutylene or not more than 2 mol per mol of t-butyl alcohol.

3. The process according to claim 1, wherein the contact is effected at a temperature of 300° to 450° C.

4. The process according to claim 1, wherein the contact is effected under a gauge pressure of not more than 4 kg/cm$^2$.

5. The process according to claim 1, wherein the contact is effected with a space velocity of 500 to 6000 hr$^{-1}$.

6. The process according to claim 1, wherein the amount of molecular oxygen in the gaseous mixture is 2.0 to 4.5 mol per mol of isobutylene and/or t-butyl alcohol.

7. The process according to claim 1, wherein the gaseous mixture further comprises an inert diluent gas.

8. The process according to claim 7, wherein the amount of the inert diluent gas in the gaseous mixture is 10 to 40 per mol of isobutylene and/or t-butyl alcohol.

9. The process according to claim 7, wherein the amount of the inert diluent gas in the gaseous mixture is 3.8 to 10 mol per mol of molecular oxygen.

10. The process according to claim 7, wherein the inert diluent gas is carbon dioxide or nitrogen, or their mixture.

11. The process according to claim 1, wherein t-butyl alcohol is used in the form of its azeotropic mixture with water.

* * * * *